United States Patent [19]

Roe et al.

[11] Patent Number: 5,516,674
[45] Date of Patent: May 14, 1996

[54] INSECTICIDE RESISTANCE ASSOCIATED CYTOCHROME 450

[75] Inventors: Richard M. Roe, Cary; Ernest Hodgson, Raleigh; Randy L. Rose, Clayton, all of N.C.

[73] Assignee: North Carolina State University, Raleigh, N.C.

[21] Appl. No.: 298,426

[22] Filed: Aug. 30, 1994

Related U.S. Application Data

[63] Continuation-in-part of Ser. No. 114,614, Aug. 31, 1993, abandoned.
[51] Int. Cl.$^6$ .............................. C12N 9/02; C12N 15/53; C12N 15/63; C12N 1/21; C12N 1/19
[52] U.S. Cl. ................. 435/189; 435/252.3; 435/252.31; 435/252.34; 435/320.1; 536/23.2
[58] Field of Search ............................. 435/320.1, 252.3, 435/252.33, 252.34, 254.11, 252.31, 189, 172.3; 536/23.2

[56] References Cited

U.S. PATENT DOCUMENTS 5,240,831   8/1993   Barnes .................................... 435/69.1

FOREIGN PATENT DOCUMENTS 0172506   2/1986   European Pat. Off. .

OTHER PUBLICATIONS

D. A. Wolfenbarger et al.; *LD$_{50}$ Values of Methyl Parathion and Endrin to Tobacco Budworms and Bollworms Collected in the Americas and Hyupothesis on the Spread of Resistance in These Lepidopterans to These Insecticides; Journal of Economic Entomology 66,* pp. 211–216 (1973).
M. Alexander, *Pesticides, Introduction to Soil Microbiology* 2d Ed. 1977, pp. 438–456.
W. C. Dauterman and Ernest Hodgson *Detoxication Mechanisms in Insects Biochemistry of Insects* pp. 541–577 (1978).
C. Mouches et al., *Amplification of an Esterase Gene is Responsible for Insecticide Resistance in a California Culex Mosquito, Science 233,* 778–780 (1986).
D. M. Helfman and S. H. Hughes; [50] *Use of Antibodies to Screen cDNA Expression Libraries Prepared in Plasmid Vectors; Methods in Enzymology 152,* pp. 451–457 (1987).
S. J. Gould et al; *Use of the DNA polymerase chain reaction for homology probing; Isolation of partial cDNA or genomic clones encoding the iron–sulfur protein of succinate dehydrogenase from several species; Proc. Natl. Acad. Sci. 86;* pp. 1934–1938 (1989).

S. S. Sundseth et al; *Monoclonal Antibodies to Resistance–Related Forms of Cytochrome P450 in Drosophila melanogaster; Pesticide Biochemistry and Physiology 33;* pp. 176–188 (1989).
E. Hodgson, R. M. Roe, and N. Motoyama, *Pesticide–Microbial Interactions in Soil In Pesticides and the Future: Toxicological Studies of Risks and Benefits,* Eds. Joel R. Coats and L. Somasundaram 1991 pp. 23–30.
M. B. Cohen et al; *A host–inducible cytochrome P–450 from a host–specific caterpillar; Molecular cloning and evolution; Proc. Natl. Acad. Sci. 89;* pp. 10920–10924 (1992).
Dowd (1990) Responses of representative midgut detoxifying enzymes from *Heliothis zea* and *Spodoptera frugiperda* to trichothecenes. Insect Biochem 20:349–356.
Hodgson et al. (1991) Insect cytochrome P450 in NATO ASI series, series A, Life sciences. Molecular aspects of monooxygenases and bioactivation of toxic compounds; Arinc et al. (ed.) Plenum press:New York. 202:75–92.
Yu et al. (1993) Induction of detoxification enzymes in phytophagous insects:roles of insecticide synergists, larval age and species. Archives Insect Biochem. Physiol 24:21–32.
McCaffery et al. (1991) Enzymes and resistance to insecticides in *Heliothis virescens* Biochem Soc Trans. 19:762–767.
Berenbaum et al. (1992) Cytochrome P450 monooxygenase genes in oligophagous Lepidoptera in ACS Symposium Series. Molecular mechanisms of insecticide resistance. Mullin et al. (ed.) American Chemical Society:Washington D.C. 505:114–124.

*Primary Examiner*—Robert A. Wax
*Assistant Examiner*—G. Bugaisky
*Attorney, Agent, or Firm*—Bell, Seltzer, Park & Gibson

[57] ABSTRACT

Disclosed are microbial cells useful for degrading insecticides and chlorinated organics and for the production of a protein which degrades insecticides and chlorinated organics, which microbial cells contain and express a heterologous DNA molecule encoding an insect detoxication protein (e.g., an esterase, a cytochrome p450, a glutathione transferase). Preferably, the host cell is a bacteria which grows in soil (e.g., is from the genera *Pseudomonas* or *Bacillus*). Methods of using the cells and proteins and compositions thereof are also disclosed.

8 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

(A) LENGTH: 1448 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Heliothis virescens (xi) SEQUENCE DESCRIPTION: SEQ ID NO:1:

| | | | | | | |
|---|---|---|---|---|---|---|
| TAGTTCTCGA | CGTGGACACT | GTCAAGAGGA | TCACCGTCAA | AGACTTTGAA | CATTTCGTTG | 60 |
| ACAGGCGAAC | GTTCACCAGC | AGCTTTGATC | CCATCTTTGG | AAGAGGGCTG | CTGTTGCTAC | 120 |
| ATGGTGACGA | ATGGAAAGCA | ATGCGGTCTA | CGATGAGTCC | AGCGTTCACC | AGCTCCAAGA | 180 |
| TGCGCCTGAT | GGTGCCCTTC | ATGGAGGAGA | TCGCTTTGGA | AATGATTAGA | GTACTCCGGG | 240 |
| GGAAGATCAA | GGATTCTGGG | AAACCTTACA | TCGACGTGGA | AGCCAAGAGT | ATGATGACCA | 300 |
| GGTACGCGAA | TGACGTCATA | GCCTCATGCG | CCTTCGGGTT | GAAAGTGAAC | TCCCAGGCGT | 360 |
| CGGACCACGA | GTTTTATGTC | AACAGTCAAG | CTATCACCAA | GTTTAAGTTT | TCAGCCTTTC | 420 |
| TGAAGGTCCT | GTTCTTTAGA | TGCCTGCCGA | GTGTTGCTCA | GAAGCTGAAG | ATGTCATTGG | 480 |
| TGCCACGTGA | GTGTTCAGAC | TACTTCTCAA | ATGTGGTGCT | GACCACGATG | AAGGACAGAG | 540 |
| AGAAGAACAA | GGTCGTACGA | AATGACCTCA | TCAACATTCT | GATGGAAGTG | AAGAAAGGTC | 600 |
| AACTGACTCA | CGAAAAAGAT | GACGCCGATG | CTGACGCTGG | GTTTGCAACA | GTAGAAGAGT | 660 |
| CACACATTGG | TAGAAAGCAA | CACAATTATG | AATGGACAGA | CTCGGACCTA | ATAGCGCAAG | 720 |
| CAGCGTTATT | CCTATTCGCC | GGCTTCGACA | CAGTTTCCAC | ATCCATGTCG | TTCCTACTGT | 780 |
| ACGAATTGGC | AGTCAACCCT | GATGTGCAGG | ACAGGCTGCA | GGAGATCAGG | GAGTATGATG | 840 |
| AGAAGAACCA | TGGGAAGATT | GATTATAATG | TCGTTCAGAG | CATGACATAT | TTGGATATGG | 900 |
| TGGTTTCTGA | GGGTTTGCGA | CTATGGCCCC | CAGCTGCAGT | CGTAGACAGA | GTCTGTGTGA | 960 |
| AAGACTACAA | TATCGGAAGA | CCCAATAAAA | AGGCCACAAA | AGATTTGATC | ATTCACACGG | 1020 |
| GCCAGGCTGT | GGCAATATCT | CCCTGGTTGT | TCCACAGGAA | CCCGAAGTTT | TTCCCCGAAC | 1080 |
| CCGCCAAGTT | CGACCCTGAA | AGGTTTCACC | AGAAAACAAG | ACACAAAATC | CAACCTTTTA | 1140 |
| CCTATTTTCC | TTTTGCCTGG | GGCCAAGGAA | TTGTATCGGT | TCTCGTTTCG | CACTTTGTGA | 1200 |
| AATCAAAGTA | ATACTGTACC | TGCTCATTCG | GGAGATGGAA | GTATACCCCT | TCGAGAAGAC | 1260 |
| AATATATCCT | CCACAGTTGT | CTAAAGACCG | ATTTAACATG | CACTTAGAGG | GAGGCGCCTG | 1320 |
| GGTCAGGCTT | CGAGTTCGTC | CAGAAAAATC | TTAATTAGGT | GTATTAACTT | GTGATTTTAT | 1380 |
| TTTATTTAAA | TATATTTTAT | TATGAATAAA | TATTGTGCAT | TTATGTATAC | AAAAAAAAAA | 1440 |
| AAAAAAAA | | | | | | 1448 |

(2) INFORMATION FOR SEQ ID NO:2:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (v) FRAGMENT TYPE: N-terminal (vi) ORIGINAL SOURCE:
(A) ORGANISM: Heliothis virescens (xi) SEQUENCE DESCRIPTION: SEQ ID NO:2:

```
Asp Asp Glu Xaa Arg Glu Val Arg Thr Ala Gln Gly Pro Leu Arg Gly
 1           5                   10                      15
```

( 2 ) INFORMATION FOR SEQ ID NO:3:

( i ) SEQUENCE CHARACTERISTICS:
        ( A ) LENGTH: 1776 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Heliothis virescens ( i x ) FEATURE:
        ( A ) NAME/KEY: CDS
        ( B ) LOCATION: 103..1680

( x i ) SEQUENCE DESCRIPTION: SEQ ID NO:3:

```
AGATCACGCC AGTCAGTCAC AGTCACGGTC ACAACAAGTG CGCGCGCGCT GTCTCTCAGT        60

TATTTGGTTT CTGTTTCTCG CAGCCATGAT TCTGCTTCTA AC ATG GCT GGT GGT         114
                                              Met Ala Gly Gly
                                               1

GAT CAT CAC AGC GGT CCT GCT GTA CTT CCG AAG CGT GTA CAG CCA ACT        162
Asp His His Ser Gly Pro Ala Val Leu Pro Lys Arg Val Gln Pro Thr
 5               10                  15                      20

GTC CAA GCA GGG GGT GAA CCA CCT CCC CAC GAT CCC AGT CTT GGG AAC        210
Val Gln Ala Gly Gly Glu Pro Pro Pro His Asp Pro Ser Leu Gly Asn
             25                  30                      35

CTG ATG TGG ATG GTC ATG AAG CAG GAG CAC TTC GTT GAT ACC CTG GGG        258
Leu Met Trp Met Val Met Lys Gln Glu His Phe Val Asp Thr Leu Gly
             40                  45                      50

CGG TGT GTC AAG GCT TTT CCT GAT GAT AAG ATA GTA GGA CAC TAC GAC        306
Arg Cys Val Lys Ala Phe Pro Asp Asp Lys Ile Val Gly His Tyr Asp
         55                  60                  65

ATG GTG AGC CCT ATC TTG GTA GTT CTC GAC GTG GAC ACT GTC AAG AGG        354
Met Val Ser Pro Ile Leu Val Val Leu Asp Val Asp Thr Val Lys Arg
         70                  75                  80

ATC ACC GTC AAA GAC TTT GAA CAT TTC GTT GAC AGG CGA ACG TTC ACC        402
Ile Thr Val Lys Asp Phe Glu His Phe Val Asp Arg Arg Thr Phe Thr
 85                  90                  95                 100

AGC AGC TTT GAT CCC ATC TTT GGA AGA GGG CTG CTG TTG CTA CAT GGT        450
Ser Ser Phe Asp Pro Ile Phe Gly Arg Gly Leu Leu Leu Leu His Gly
                105                 110                 115

GAC GAA TGG AAA GCA ATG CGG TCT ACG ATG AGT CCA GCG TTC ACC AGC        498
Asp Glu Trp Lys Ala Met Arg Ser Thr Met Ser Pro Ala Phe Thr Ser
             120                 125                 130

TCC AAG ATG CGC CTG ATG GTG CCC TTC ATG GAG GAG ATC GCT TTG GAA        546
Ser Lys Met Arg Leu Met Val Pro Phe Met Glu Glu Ile Ala Leu Glu
         135                 140                 145

ATG ATT AGA GTA CTC CGG GGG AAG ATC AAG GAT TCT GGG AAA CCT TAC        594
Met Ile Arg Val Leu Arg Gly Lys Ile Lys Asp Ser Gly Lys Pro Tyr
 150                 155                 160

ATC GAC GTG GAA GCC AAG AGT ATG ATG ACC AGG TAC GCG AAT GAC GTC        642
Ile Asp Val Glu Ala Lys Ser Met Met Thr Arg Tyr Ala Asn Asp Val
165                 170                 175                 180

ATA GCC TCA TGC GCC TTC GGG TTG AAA GTG AAC TCC CAG GCG TCG GAC        690
Ile Ala Ser Cys Ala Phe Gly Leu Lys Val Asn Ser Gln Ala Ser Asp
             185                 190                 195

CAC GAG TTT TAT GTC AAC AGT CAA GCT ATC ACC AAG TTT AAG TTT TCA        738
His Glu Phe Tyr Val Asn Ser Gln Ala Ile Thr Lys Phe Lys Phe Ser
         200                 205                 210
```

| | | | | | | | | | | | | | | | | |
|---|---|---|---|---|---|---|---|---|---|---|---|---|---|---|---|---|
| GCC | TTT | CTG | AAG | GTC | CTG | TTC | TTT | AGA | TGC | CTG | CCG | AGT | GTT | GCT | CAG | 786 |
| Ala | Phe | Leu | Lys | Val | Leu | Phe | Phe | Arg | Cys | Leu | Pro | Ser | Val | Ala | Gln | |
| | | 215 | | | | 220 | | | | | 225 | | | | | |
| AAG | CTG | AAG | ATG | TCA | TTG | GTG | CCA | CGT | GAG | TGT | TCA | GAC | TAC | TTC | TCA | 834 |
| Lys | Leu | Lys | Met | Ser | Leu | Val | Pro | Arg | Glu | Cys | Ser | Asp | Tyr | Phe | Ser | |
| | 230 | | | | | 235 | | | | 240 | | | | | | |
| AAT | GTG | GTG | CTG | ACC | ACG | ATG | AAG | GAC | AGA | GAG | AAG | AAC | AAG | GTC | GTA | 882 |
| Asn | Val | Val | Leu | Thr | Thr | Met | Lys | Asp | Arg | Glu | Lys | Asn | Lys | Val | Val | |
| 245 | | | | | 250 | | | | | 255 | | | | | 260 | |
| CGA | AAT | GAC | CTC | ATC | AAC | ATT | CTG | ATG | GAA | GTG | AAG | AAA | GGT | CAA | CTG | 930 |
| Arg | Asn | Asp | Leu | Ile | Asn | Ile | Leu | Met | Glu | Val | Lys | Lys | Gly | Gln | Leu | |
| | | | | 265 | | | | | 270 | | | | | 275 | | |
| ACT | CAC | GAA | AAA | GAT | GAC | GCC | GAT | GCT | GAC | GCT | GGG | TTT | GCA | ACA | GTA | 978 |
| Thr | His | Glu | Lys | Asp | Asp | Ala | Asp | Ala | Asp | Ala | Gly | Phe | Ala | Thr | Val | |
| | | | 280 | | | | 285 | | | | | 290 | | | | |
| GAA | GAG | TCA | CAC | ATT | GGT | AGA | AAG | CAA | CAC | AAT | TAT | GAA | TGG | ACA | GAC | 1026 |
| Glu | Glu | Ser | His | Ile | Gly | Arg | Lys | Gln | His | Asn | Tyr | Glu | Trp | Thr | Asp | |
| | | 295 | | | | 300 | | | | | 305 | | | | | |
| TCG | GAC | CTA | ATA | GCG | CAA | GCA | GCG | TTA | TTC | CTA | TTC | GCC | GGC | TTC | GAC | 1074 |
| Ser | Asp | Leu | Ile | Ala | Gln | Ala | Ala | Leu | Phe | Leu | Phe | Ala | Gly | Phe | Asp | |
| | 310 | | | | | 315 | | | | | 320 | | | | | |
| ACA | GTT | TCC | ACA | TCC | ATG | TCG | TTC | CTA | CTG | TAC | GAA | TTG | GCA | GTC | AAC | 1122 |
| Thr | Val | Ser | Thr | Ser | Met | Ser | Phe | Leu | Leu | Tyr | Glu | Leu | Ala | Val | Asn | |
| 325 | | | | | 330 | | | | | 335 | | | | | 340 | |
| CCT | GAT | GTG | CAG | GAC | AGG | CTG | CTG | CAG | GAG | ATC | AGG | GAG | TAT | GAT | GAG | 1170 |
| Pro | Asp | Val | Gln | Asp | Arg | Leu | Leu | Gln | Glu | Ile | Arg | Glu | Tyr | Asp | Glu | |
| | | | | 345 | | | | | 350 | | | | | 355 | | |
| AAG | AAC | CAT | GGG | AAG | ATT | GAT | TAT | AAT | GTC | GTT | CAG | AGC | ATG | ACA | TAT | 1218 |
| Lys | Asn | His | Gly | Lys | Ile | Asp | Tyr | Asn | Val | Val | Gln | Ser | Met | Thr | Tyr | |
| | | | 360 | | | | | 365 | | | | | 370 | | | |
| TTG | GAT | ATG | GTG | GTT | TCT | GAG | GGT | TTG | CGA | CTA | TGG | CCC | CCA | GCT | GCA | 1266 |
| Leu | Asp | Met | Val | Val | Ser | Glu | Gly | Leu | Arg | Leu | Trp | Pro | Pro | Ala | Ala | |
| | | | 375 | | | | 380 | | | | | 385 | | | | |
| GTC | GTA | GAC | AGA | GTC | TGT | GTG | AAA | GAC | TAC | AAT | ATC | GGA | AGA | CCC | AAT | 1314 |
| Val | Val | Asp | Arg | Val | Cys | Val | Lys | Asp | Tyr | Asn | Ile | Gly | Arg | Pro | Asn | |
| | 390 | | | | | 395 | | | | | 400 | | | | | |
| AAA | AAG | GCC | ACA | AAA | GAT | TTG | ATC | ATT | CAC | ACG | GGC | CAG | GCT | GTG | GCA | 1362 |
| Lys | Lys | Ala | Thr | Lys | Asp | Leu | Ile | Ile | His | Thr | Gly | Gln | Ala | Val | Ala | |
| 405 | | | | | 410 | | | | | 415 | | | | | 420 | |
| ATA | TCT | CCC | TGG | TTG | TTC | CAC | AGG | AAC | CCG | AAG | TTT | TTC | CCC | GAA | CCC | 1410 |
| Ile | Ser | Pro | Trp | Leu | Phe | His | Arg | Asn | Pro | Lys | Phe | Phe | Pro | Glu | Pro | |
| | | | | 425 | | | | | 430 | | | | | 435 | | |
| GCC | AAG | TTC | GAC | CCT | GAA | AGG | TTT | TCA | CCA | GAA | AAC | AGA | CAC | AAA | ATC | 1458 |
| Ala | Lys | Phe | Asp | Pro | Glu | Arg | Phe | Ser | Pro | Glu | Asn | Arg | His | Lys | Ile | |
| | | | 440 | | | | | 445 | | | | | 450 | | | |
| CTT | CCT | TTT | ACC | TAT | TTT | TCC | TTT | TGC | CTG | GGG | CCA | AGG | AAT | TGT | ATC | 1506 |
| Leu | Pro | Phe | Thr | Tyr | Phe | Ser | Phe | Cys | Leu | Gly | Pro | Arg | Asn | Cys | Ile | |
| | | 455 | | | | | 460 | | | | | 465 | | | | |
| GGT | TCT | CGT | TTC | GCA | CTT | TGT | GAA | ATC | AAA | GTA | ATA | CTG | TAC | CTG | CTC | 1554 |
| Gly | Ser | Arg | Phe | Ala | Leu | Cys | Glu | Ile | Lys | Val | Ile | Leu | Tyr | Leu | Leu | |
| | | 470 | | | | | 475 | | | | | 480 | | | | |
| ATT | CGG | GAG | ATG | GAA | GTA | TAC | CCC | TTC | GAG | AAG | ACA | ATA | TAT | CCT | CCA | 1602 |
| Ile | Arg | Glu | Met | Glu | Val | Tyr | Pro | Phe | Glu | Lys | Thr | Ile | Tyr | Pro | Pro | |
| 485 | | | | | 490 | | | | | 495 | | | | | 500 | |
| CAG | TTG | TCT | AAA | GAC | CGA | TTT | AAC | ATG | CAC | TTA | GAG | GGA | GGC | GCC | TGG | 1650 |
| Gln | Leu | Ser | Lys | Asp | Arg | Phe | Asn | Met | His | Leu | Glu | Gly | Gly | Ala | Trp | |
| | | | | 505 | | | | | 510 | | | | | 515 | | |
| GTC | AGG | CTT | CGA | GTT | CGT | CCA | GAA | AAA | TCT | TAATTAGGTG | TATTAACTTG | | | | | 1700 |
| Val | Arg | Leu | Arg | Val | Arg | Pro | Glu | Lys | Ser | | | | | | | |
| | | 520 | | | | | 525 | | | | | | | | | |

```
TGATTTTATT TTATTTAAAT ATATTTTATT ATGAATAAAT ATTGTGCATT TATGTATACA    1760

AAAAAAAAAA AAAAA                                                    1776
```

( 2 ) INFORMATION FOR SEQ ID NO:4:

( i ) SEQUENCE CHARACTERISTICS:
        ( A ) LENGTH: 526 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Gly  Gly  Asp  His  His  Ser  Gly  Pro  Ala  Val  Leu  Pro  Lys  Arg
 1              5                        10                       15

Val  Gln  Pro  Thr  Val  Gln  Ala  Gly  Gly  Glu  Pro  Pro  Pro  His  Asp  Pro
               20                       25                       30

Ser  Leu  Gly  Asn  Leu  Met  Trp  Met  Val  Met  Lys  Gln  Glu  His  Phe  Val
          35                        40                       45

Asp  Thr  Leu  Gly  Arg  Cys  Val  Lys  Ala  Phe  Pro  Asp  Asp  Lys  Ile  Val
     50                        55                       60

Gly  His  Tyr  Asp  Met  Val  Ser  Pro  Ile  Leu  Val  Val  Leu  Asp  Val  Asp
65                  70                       75                            80

Thr  Val  Lys  Arg  Ile  Thr  Val  Lys  Asp  Phe  Glu  His  Phe  Val  Asp  Arg
               85                       90                            95

Arg  Thr  Phe  Thr  Ser  Ser  Phe  Asp  Pro  Ile  Phe  Gly  Arg  Gly  Leu  Leu
               100                      105                      110

Leu  Leu  His  Gly  Asp  Glu  Trp  Lys  Ala  Met  Arg  Ser  Thr  Met  Ser  Pro
          115                      120                      125

Ala  Phe  Thr  Ser  Ser  Lys  Met  Arg  Leu  Met  Val  Pro  Phe  Met  Glu  Glu
     130                      135                      140

Ile  Ala  Leu  Glu  Met  Ile  Arg  Val  Leu  Arg  Gly  Lys  Ile  Lys  Asp  Ser
145                      150                      155                      160

Gly  Lys  Pro  Tyr  Ile  Asp  Val  Glu  Ala  Lys  Ser  Met  Met  Thr  Arg  Tyr
                    165                      170                      175

Ala  Asn  Asp  Val  Ile  Ala  Ser  Cys  Ala  Phe  Gly  Leu  Lys  Val  Asn  Ser
               180                      185                      190

Gln  Ala  Ser  Asp  His  Glu  Phe  Tyr  Val  Asn  Ser  Gln  Ala  Ile  Thr  Lys
          195                      200                      205

Phe  Lys  Phe  Ser  Ala  Phe  Leu  Lys  Val  Leu  Phe  Phe  Arg  Cys  Leu  Pro
     210                      215                      220

Ser  Val  Ala  Gln  Lys  Leu  Lys  Met  Ser  Leu  Val  Pro  Arg  Glu  Cys  Ser
225                      230                      235                      240

Asp  Tyr  Phe  Ser  Asn  Val  Val  Leu  Thr  Thr  Met  Lys  Asp  Arg  Glu  Lys
                    245                      250                      255

Asn  Lys  Val  Val  Arg  Asn  Asp  Leu  Ile  Asn  Ile  Leu  Met  Glu  Val  Lys
               260                      265                      270

Lys  Gly  Gln  Leu  Thr  His  Glu  Lys  Asp  Asp  Ala  Asp  Ala  Asp  Ala  Gly
          275                      280                      285

Phe  Ala  Thr  Val  Glu  Glu  Ser  His  Ile  Gly  Arg  Lys  Gln  His  Asn  Tyr
     290                      295                      300

Glu  Trp  Thr  Asp  Ser  Asp  Leu  Ile  Ala  Gln  Ala  Ala  Leu  Phe  Leu  Phe
305                      310                      315                      320

Ala  Gly  Phe  Asp  Thr  Val  Ser  Thr  Ser  Met  Ser  Phe  Leu  Leu  Tyr  Glu
                    325                      330                      335
```

| | | | | | | | | | | | | | |
|---|---|---|---|---|---|---|---|---|---|---|---|---|---|
| Leu | Ala | Val | Asn 340 | Pro | Asp | Val | Gln | Asp 345 | Arg | Leu | Leu | Gln | Glu 350 | Ile | Arg |
| Glu | Tyr | Asp 355 | Glu | Lys | Asn | His | Gly 360 | Lys | Ile | Asp | Tyr | Asn 365 | Val | Val | Gln |
| Ser | Met 370 | Thr | Tyr | Leu | Asp | Met 375 | Val | Val | Ser | Glu | Gly 380 | Leu | Arg | Leu | Trp |
| Pro 385 | Pro | Ala | Ala | Val | Val 390 | Asp | Arg | Val | Cys | Val 395 | Lys | Asp | Tyr | Asn | Ile 400 |
| Gly | Arg | Pro | Asn | Lys 405 | Lys | Ala | Thr | Lys | Asp 410 | Leu | Ile | Ile | His | Thr 415 | Gly |
| Gln | Ala | Val | Ala 420 | Ile | Ser | Pro | Trp | Leu 425 | Phe | His | Arg | Asn | Pro 430 | Lys | Phe |
| Phe | Pro | Glu 435 | Pro | Ala | Lys | Phe | Asp 440 | Pro | Glu | Arg | Phe | Ser 445 | Pro | Glu | Asn |
| Arg | His 450 | Lys | Ile | Leu | Pro | Phe 455 | Thr | Tyr | Phe | Ser | Phe 460 | Cys | Leu | Gly | Pro |
| Arg 465 | Asn | Cys | Ile | Gly | Ser 470 | Arg | Phe | Ala | Leu | Cys 475 | Glu | Ile | Lys | Val | Ile 480 |
| Leu | Tyr | Leu | Leu | Ile 485 | Arg | Glu | Met | Glu | Val 490 | Tyr | Pro | Phe | Glu | Lys 495 | Thr |
| Ile | Tyr | Pro | Pro 500 | Gln | Leu | Ser | Lys | Asp 505 | Arg | Phe | Asn | Met | His 510 | Leu | Glu |
| Gly | Gly | Ala 515 | Trp | Val | Arg | Leu | Val 520 | Arg | Pro | Glu | Lys 525 | Ser | | | |

INSECTICIDE RESISTANCE ASSOCIATED CYTOCHROME 450

RELATED APPLICATIONS

This application is a continuation-in-part of application Ser. No. 08/114,614, filed Aug. 31, 1993 now abandoned.

FIELD OF THE INVENTION

This invention concerns the degradation of pesticides and chlorinated organic compounds with proteins derived from insects which are resistant to pesticides and microbacteria containing DNA encoding the same.

BACKGROUND OF THE INVENTION

For eons of time insects have been in natural competition with plants. Insects depend on plants for food and consequently threaten the plants' survival. Plants develop new chemical insecticides to protect themselves from the insects. The insects, in turn, develop new methods to metabolize the plant insecticides.

The ability of insects populations to rapidly adapt to pesticides is also apparent today, as many insects of agricultural and medical importance have become resistant to control with man-made insecticides. No class of insecticide chemistry has been exempt from this process, and, as insecticides have become widely used, a variety of insecticide-selected insect genes with unique properties toward chemical metabolism have developed.

In contrast to insects, soil-inhabiting microorganisms have not been exposed to this type of environmental pressure, and generally have not developed mechanisms of degrading insecticides like that of insects. Thus, many insecticides (e.g., Aldrin, Chlordane, DDT, HCH) are notoriously persistent in soil (See, e.g., R. Stanier et al., *The Microbial World*, 557–58 (5th Ed. 1986)). Such persistent insecticides are referred to as "recalcitrant insecticides," and have half lives in soil which are measured in periods of years, rather than periods of days. See M. Alexander, *Introduction to Soil Microbiology*, pg. 445 (2d Ed. 1977).

Insecticides are critically important to modern agriculture. Their value is offset, however, by the tendency of soil to become contaminated for prolonged periods of time with insecticides which are no longer effective in controlling insects. There is a continued need for new solutions to this problem.

SUMMARY OF THE INVENTION

In view of the foregoing, an object of this invention is to take advantage of the special ability of insects to evolve proteins which make them resistant to insecticides for practical, commercial applications in the degradation of such insecticides. Moreover, because of the similar chemistry of insecticides and chlorinated organic pollutants, the instant invention provides useful methods for degrading chlorinated organic compounds.

Accordingly, a first aspect of the present invention is a microbial cell useful for degrading insecticides and chlorinated organics and for the production of a protein which degrades insecticides and chlorinated organics, which microbial host cell contains and expresses a heterologous DNA molecule encoding an insect detoxication protein (e.g., an esterase, a cytochrome p450, a glutathione transferase). Preferably, the host cell is a bacteria which grows in soil (e.g., is from the genera *Pseudomonas* or *Bacillus*).

In one particular embodiment of the foregoing, the DNA is (a) DNA encoding Tobacco Budworm (*Heliothis virescens* (F)) insecticide resistance-associated fat body cytochrome P450 and comprising the sequence given herein as SEQ ID NO:3; (b) DNA such as insect DNA which hybridizes to DNA of (a) above and encodes an insecticide resistance-associated cytochrome P450; and (c) DNA which encodes a insecticide resistance-associated cytochrome P450 encoded by (a) or (b) above and which differs from the DNA (a) or (b) above due to the degeneracy of the genetic code.

A second aspect of the present invention is a composition useful for the degradation of insecticides and chlorinated organics. The composition comprises, in combination, a microbial cell as described above and an agriculturally acceptable carrier.

A third aspect of the present invention is a method for the degradation of insecticides and chlorinated organics, comprising contacting (e.g., in a bioreactor) a microbial cell as described above with a liquid substrate such as an aqueous waste effluent stream which is contaminated with an insecticide or chlorinated organic, the microbial cell being present in an amount effective to degrade the toxic agent.

A fourth aspect of the present invention is a method for the degradation of insecticides and chlorinated organics. The method comprises applying a microbial cell as described above to a solid substrate contaminated therewith (e.g., soil) in an amount effective to degrade the insecticide or chlorinated organic.

A fifth aspect of the present invention is a composition useful for the degradation of insecticides and chlorinated organics comprising, in combination, an insect detoxication protein and an agriculturally acceptable carrier.

A sixth aspect of the present invention is a method for the degradation of insecticides and chlorinated organics, comprising applying an insect detoxication protein to an insecticide-contaminated substrate in an amount effective to degrade said insecticide.

Also disclosed herein is a method of combatting insects in a location comprising the steps of (a) applying to that location an insecticide effective against that insect, and (b) applying to that location an agent for degrading that insecticide selected from the group consisting of (i) an insect detoxication protein in an amount effective to degrade the applied insecticide, (ii) a microbial cell as described above in an amount effective to degrade the applied insecticide.

The foregoing and other objects and aspects of the present invention are explained in detail in the specification hereinbelow.

DETAILED DESCRIPTION OF THE INVENTION

An advantage of the present invention is that it combines the fields of entomology, soil microbiology, agricultural formulations, and basic molecular biology techniques to enable the production and use of a variety of new products. These areas are discussed in brief below. While the present invention is useful for degrading insecticides and chlorinated organics in soil and in liquid substrates, the invention is particularly useful for degrading recalcitrant insecticides (i.e., insecticides having typical half lives in soil of 1, 2, or 3 years or more).

A. Insect Detoxication Proteins

Insect detoxication proteins employed in carrying out the present invention may be from any suitable species of origin.

Insects, in general, are in the class Insecta of the phylum Arthropoda. Illustrative of insects sources of detoxication proteins at the level of Order include, but are not limited to, Thysanura, Ephemerida, Odonta, Orthoptera, Hemiptera, Coleoptera, Hymenoptera, Diptera, Trichoptera, and Lepidoptera. Particular examples include, but are not limited to, *Heliothis* species such as *Heliothis virescens* (Tobacco budworm), *Culex tarsalis* (mosquito), *Musca domestica* (housefly), *Chrysoma putoria* (blow flies), *Cimex lectularius* (bedbugs), *Tribolium castaneum* (rust-red flour beetles), *Tetranychus urticae* (spider mites), *Oncopeltus fasciatus* (milkweed bug), *Trichoplusia ni* (Cabbage looper), *Blattella germanica* (German cockroach), *Prodenia eridania* (southern armyworm), *Tenebrio molitor* (mealworm), *Calliphora erythrocephala* (blow fly), *Schistocerca gregaria* (locust), *Bombyx mori* (silkworm), *Costelytra zealandica* (grass grubs), *Periplaneta americana* (American roach), and *Blaberus craniifver* (giant roach).

The term "insect," as used herein to refer to a source of an insect detoxication protein, is also intended to encompass arachnids (i.e., members of the class Arachnida), such as spiders, ticks, mites, etc. Illustrative species of mites include, but are not limited to, plant feeding mites in the family Tetranychidae, such as the six-spotted spider mite (*Eotetranychus sexmaculatus*), the Texas citrus mite (*Eutetranychus banksi*), the European red mite (*Panonychus ulmi*), the McDaniel mite (*Tetranychus mcdanieli*), the Pacific spider mite (*Tetranychus pacificus*), the Strawberry spider mite (*Tetranychus turkestani*), the twospotted spider mite (*Tetranychus urticae*), the Spruce spider mite (*Oligonychus ununguis*), the Sugi spider mite (*Oligonychus hondoensis*), and *Tetranychus evansi*.

Detoxication proteins directed against any insecticide may be used in carrying out the present invention. For example, the protein may be one which imparts resistance to organophosphorus insecticides (e.g., S,S,S-tributy phosphorotrithiote, malathion, acephate, methyl parathion, methidathion, diazinon, azinphosmethyl, and monocrotphos), carbamate pesticides (e.g., thiodicarb), pyrethroid pesticides (e.g., cypermethrin), and other insecticides such as DDT, endrin, carbaryl, parathionb, and EPN.

Chlorinated organics which may be degraded by the method of the present invention are chlorinated and polychlorinated hydrocarbons, and particularly chlorinated and polychlorinated aromatic hydrocarbon molecules such as the polychlorinated biphenyls (PCBs).

Any detoxication protein which imparts resistance to one or more insecticides in an insect may be employed in carrying out the present invention. Examples of proteins which serve as detoxication proteins involved in insecticide resistance include, but are not limited to, proteinases, esterases, cytochrome p450s, glutathione transferases, DDT-dehydrochlorinase, carboxylesterases, and epoxide hydrolases. For degrading chlorinated organics, the glutathione transferases are preferred. The mechanism by which the protein carries out detoxication is not critical, whether it be by conversion of the insecticide to a nontoxic or less toxic substance, conversion of the insecticide into simple products, conjugation or complex formation, or any other suitable mechanism or combination thereof.

B. DNAs Encoding Insect Detoxication Proteins

DNAs encoding insect detoxication proteins may be obtained by a variety of means known to those skilled in the art, such as the use of degenerate primers designed from the sequencing of purified detoxication proteins, expression cloning, and in situ hybridization with a DNA (or appropriate fragment thereof) which encodes an insect detoxication protein.

Hybridization conditions which will permit other DNA sequences which code on expression for a detoxication protein to hybridize to a DNA sequence encoding an insect detoxication protein are, in general, high stringency conditions. For example, hybridization of such sequences may be carried out under conditions represented by a wash stringency of 0.3M NaCl, 0.03M sodium citrate, 0.1% SDS at 60° C. or even 70° C. to DNA disclosed herein in a standard in situ hybridization assay. See J. Sambrook et al., Molecular Cloning, A Laboratory Manual (2d Ed. 1989)(Cold Spring Harbor Laboratory)). The same hybridization conditions are used to determine hybridization of oligonucleotides. In general, a second sequence which hybridizes to the first sequence will be about 70%, 75%, 80%, 85% homologous to the first sequence. The other DNA sequence is preferably insect DNA, and may be obtained from any suitable insect species (those described in Section A above being illustrative). The tissue of origin of the insect DNA is not critical, and may be obtained from sources such as the insect fat body, gut, malpighian tubules, tracheal system, nervous system, exoskeleton, muscles, etc.

Further, DNA sequences (or oligonucleotides) which code for the same detoxication protein (or fragment thereof) as coded for by the foregoing sequences, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1. Thus, when an insect detoxication protein is expressed in a non-insect host cell, the codons thereof can be optimized for expression of the protein in that host cell.

C. Genetic Engineering Techniques

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding detoxication proteins as given herein and/or to express DNA which encodes detoxication proteins as given herein. An expression vector is a replicable DNA construct in which a DNA sequence encoding a detoxication protein is operably linked to suitable control sequences capable of effecting the expression of the detoxication protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

D. Host Cells

Any suitable host cell which is a soil microbe (i.e., grows in soil) may be employed to carry out the present invention. Soil microbiology is a well-established field, and numerous reference works on this topic are available. See, e.g., E. Paul and F. Clark, *Soil Microbiology and Biochemistry* (1989); M. Alexander, *Introduction to Soil Microbiology* (2d Ed. 1977); N. Walker, *Soil Microbiology* (1975). In general, any microbe which grows in soil may be used to carry out the present invention, including procaryotes such as bacteria (including myxobacteria and actinomycetes) and cyanobacteria, and eukaryotes such as fungi (including the yeasts) and algae. All that is required is that the microbe be modified to express the detoxication protein, and that the microbe be one which grows in the soil or substrate to which it is applied.

Numerous soil bacteria are known. Thus, illustrative genera of bacteria which may be employed in carrying out the present invention include, but are not limited to, *Acinetobacter, Agrobacterium, Alcaligenes, Arthrobacter, Bacillus, Brevibacterium, Caulobacter, Cellulomonas, Clostridium, Corynebacterium, Flavobacterium, Hyphomicrobium, Metallogenium, Micrococcus, Mycobacterium, Pedomicrobium, Pseudomonas, Sarcina, Staphylococcus, Streptococcus, Xanthomonas, Myxococcus, Chondrococcus, Archangium, Polyangium, Streptomyces, Microellobosporia, Sporichthya, Nocardia, Pseudonocardia, Micromonospora, Microbispora, Micropolyspora, Thermomonospora, Thermoactinomyces, Actinobifida, Streptosporangium, Actinoplanes, Planobispora, Dactylosporangium, Geodermatophilus, Frankia,* and *Actinomyces.* M. Alexander, supra at 26, 28–29, 44.

As noted by Alexander, many soil genera of cyanobacteria have been recorded, but the ones most frequently described are *Anabaena, Calothris, Chroococcus, Cylindrospermum, Lyngbya, Microcleus, Nodularia, Nostoc, Oscillatoria, Phormidium, Plectonema, Schizothrix, Scytonema,* and *Tolypothrix.* M. Alexander, supra at 79–80. As noted by Paul and Clark, cyanobacteria are ubiquitous in their distribution, and may be divided into the orders Chamaesiphonales, Chroococcales, and Oscillatoriales. E. Paul and F. Clark, supra at 57–58. These orders and generas are illustrative, but not limiting, of cyanobacteria which may be employed in carrying out the present invention.

Illustrative genera of fungi (including yeasts) which may be employed in carrying out the present invention include, but are not limited to, *Alternaria, Aspergillus, Botryotrichum, Botrytis, Cladosporium, Curvularia, Cylindrocarpon, Epicoccum, Fusarium, Fusidium, Geotrichum, Gliocladium, Gliomastix, Graphium, Helminthosporium, Humicola, Metarrhizum, Monilia, Myrothecium, Paecilomyces, Penicillium, Rhizoctonia, Scopulariopsis, Stachybotrys, Stemphylium, Trichoderma, Trichothecium, Verticillium, Coniothyrium, Phoma, Absidia, Cunninghamella, Mortierella, ucor, Rhizopus, Zygorhynchus, Chaetomium, Thielavia, Pythium, Candida, Cryptococcus, Debaryomyces, Hansenula, Lipomyces, Pichia, Pullularia, Rhodotorula, Saccharomyces, Schizoblastosporion, Sporobolomyces, Torula, Torulaspora, Torulopsis, Trichosporon,* and *Zygosaccharomyces.* M. Alexander, supra at 61–63.

Illustrative genera of algae (including, but not limited to, green algae and diatoms) which may be employed in carrying out the present invention include, but are not limited to, *Ankistrodesmus, Characium, Chlamydomonas, Chlorella, Chlorococcum, Dactylococcus, Hormidium, Protococcus, Protosiphon, Scendesmus, Spongiochloris, Stichococcus, Ulothrix, Achnanthes, Cymbella, Fragilaria, Hantzschia, Navicula, Nitschia, Pinnularia, Surirella, Synedra, Botrydiopsis, Bumillaria, Bumilleriopsis, Heterococcus,* and *Heterothrix.* M. Alexander, supra at 79–80.

Illustrative species useful for carrying out the present invention include, but are not limited to, *Agrobacterium tumefaciens, Pseudomonas cepaciae, Bacillus thuringiensis, Bacillus popilliae, Bacillus lentimorbus, Bacillus sphaericus, Lactococcus lactis, Colletotrichum gloeosporiodes, Colletotrichum malvarum, Alternaria cassiae, Fusarium lateritium, Alternaria macrospora, Phytopthora palmavora, Alternari euphorbiicola, Saccharomyces cerevisiae, Aspergillus fumigatus, Penicillium funiculosum, Pythium aphanidermatum, Anabaena spiroides, Anabaenopsis circularis Tolypothrix tenuis, Beauveria bassiana, Metarhizium anisopliae, Hirsutella thompsonii, Nomureae rileyi, Verticillium lecanii* and *Neozygitesfloridana.* See generally M. Alexander, supra; U.S. Pat. No. 4,755,208 at Columns 1–2 (applicant specifically intends that the disclosures of all U.S. patent references cited herein be incorporated by reference in their entirety); L. Miller et al. *Bacterial, Viral, and Fungal Insecticides,* in Biotechnology and Biological Frontiers, 214 (P. Abelson, Ed. 1984); U.S. Pat. No. 4,752,469 to Kennedy.

Soil microbes employed in carrying out the present invention can be selected to correspond to those which are typically found, in nature, in the substrate to be treated, by methods well known in the art of soil microbiology. See, e.g., E. Paul and F. Clark, supra at 32–48.

Soil microbes employed in carrying out the present invention are preferably not seriously pathologic in humans, plants or animals, although microbes which are in fact pathogenic to undesireable insect pests or weeds may be employed, numerous examples of which exist in the patent literature. See, e.g., U.S. Pat. No. 4,755,207 to Bannon; U.S. Pat. No. 4,755,208 to Riley et al.

Transformed host cells are cells which have been transformed or transfected with vectors containing a DNA sequence encoding an insect detoxication protein constructed using recombinant DNA techniques. Transformed host cells ordinarily express the detoxication protein, but host cells transformed for purposes of cloning or amplifying the detoxication protein DNA do not need to express the detoxication protein.

Prokaryote host cells include gram negative or gram positive organisms, for example *Escherichia coli (E. coli)* or Bacilli. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the beta-lactamase (penicillinase) and lactose promoter systems (Chang et al., *Nature* 275,615 (1978); and Goeddel et al.,

*Nature* 281., 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). The promoter and Shine-Dalgarno sequence (for prokaryotic host expression) are operably linked to the DNA encoding the detoxication protein, i.e., they are positioned so as to promote transcription of detoxication protein messenger RNA from the DNA.

Several different systems for the expression of P450 proteins are currently in use. Heterologous expression systems have facilitated the isolation and characterization of many P450 proteins. These systems have allowed for studies of structure/function relationships through site-directed mutagenesis and the construction of chimeric proteins. The recent expansion of P450 cloning from insect systems will be particularly well suited for the utilization of expression systems, since isolation of purified insect P450s has been particularly difficult.

Many expression systems have been used in the expression of mammalian cytochrome P450s. These include yeast (Oeda et al., *Saccharomyces cerevisiae* 4, 203–210 (1985); Ching et al., *Saccharomyces cerevisiae* 42, 753–758 (1991); C. Cullin, *Saccharomyces cerevisiae* 65, 203–217 (1988)), baculovirus (Assefa et al., *Arch. Biochem. Biophys.* 274, 481–490 (1989)), COS cells (McManus et al., *Cancer Res.* 50, 3367–3376 (1990); Zuber et al., *Proc. Natl. Acad. Sci. U.S.A.* 85, 699–703 (1988)), and vaccinia virus (Aoyama et al., *Mol. Carcinog.* 2, 192–198 (1989); Liu et al., *Arch. Biochem. Biophys.* 284, 400–406 (1991); Aoyama et al., *Proc. Natl. Acad. Sci. U.S.A.* 87, 4790–4793 (1990); Aoyama et al., *Endocrinology* 126, 3101–3106 (1990)). Recently, functional P450s have been produced in *Escherichia coli*, i.e., rabbit liver P450 2El (Larson et al., *J. Biol. Chem.* 266, 7321–7324 (1991)), bovine adrenal gland P450 17A1 (Barnes et al., *Proc. Natl. Acad. Sci. U.S.A.* 88, 5597–5601 (1991)), rat liver P450 7A (Li et al., *J. Biol. Chem.* 266, 19186–19191 (1991)), human P450 1A2 (Fisher et al., *FASEB J.* 6, 759–764 (1992)) and bovine P450 11A (Wada et al., *Biophys.* 290, 376–380 (1991)).

Larson et al., *J. Biol. Chem.* 266, 7321–7324 (1991), briefly summarizes the advantages and disadvantages for several of the above mentioned expression systems. Mammalian cell lines are advantageous in that they often provide an appropriate physiological environment for the expressed P450, often including associated metabolic enzymes (Zuber et al., *Proc. Natl. Acad. Sci. U.S.A.* 234, 699–703 (1986); Crespi et al., *Carcinogenesis* 12, 1197–1201 (1989)). However, mammalian cell lines do not yield high levels of expressed protein and large scale production is difficult. In contrast, yeast are easier to culture and yield higher protein levels, however, inefficient heme incorporation has often been a difficulty in P450 expression (Oeda et al., *DNA* 4, 203–210 (1985); Yasumori et al., *Mol. Pharmacol.* 35, 443–449 (1989); Fujita et al., *DNA Cell Biol.* 9, 111–118 (1990)). Similarly, baculovirus expression also gave high yields but unacceptable levels of heine incorporation (Asseffa et al., *Arch. Biochem. Biophys.* 274, 481–490 (1989)).

The use of *E. coli* as an expression system has several advantages over other systems. Advantages include ease of culture and manipulation, availability of a wide variety of efficient vectors, and the ability to produce high levels of many heterologous proteins. Expression of hemoproteins in *E. coli* systems is the lack of internal cell membranes into which the P450 proteins can be bound. However, P450 is bound in *E. coli* to the bacterial inner membrane and retains catalytic activity (Larson et al., *J. Biol. Chem.* 266, 7321–7324 (1991); Lareson et al., *Proc. Natl. Acad. Sci.* 88, 9141–9145 (1991)).

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Eukaryotic microbes such as yeast cultures may also be transformed with vectors carrying the isolated DNA's disclosed herein. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the detoxication protein as given herein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)). Suitable vectors and promoters for use in yeast expression are further described in R. Hitzeman et al., EPO Publn. No. 73,657.

Where the host cell is used for the production of recombinant detoxication protein, the protein may be collected from the host cell and purified to the extent necessary in accordance with known techniques. See, e.g., Enzyme Purification and Related Techniques, *Methods in Enzymology* 22, 233–577 (1977).

E. Liquid Decontamination

Liquids which are contaminated with insecticides or chlorinated organic compounds are typically aqueous liquids such as contaminated groundwater or the effluent of an industrial process, such as a pulp or papermaking operation. One way such liquids are typically contacted to microorganisms as described is by passing the contaminated liquid through a bioreactor which contains the microorganism. Numerous suitable bioreactor designs are known which may be employed to carry out the instant invention. See, e.g., U.S. Pat. No. 4,655,926 to Chang et al.; U.S. Pat. No. 4,992,174 to Caplan et al.; U.S. Pat. No. 5,080,782 to Caplan et al. Examples of microbial hosts particularly suitable for bioreactors include, but are not limited to, yeast and *E. coli*. In the alternative, the microorganisms may be simply added to the liquid in an amount effective to degrade the chlorinated organic or pesticide, such as by adding the microorganism to a vat of the liquid and then, after the toxic agent is degraded, optionally autoclaving the liquid to kill the microorganism.

F. Agricultural Formulations

Agricultural formulations may, as noted above, comprise formulations of host cells as described above or formulations of detoxication proteins (the two hereafter sometimes referred to as the "active agent"). The preparation of agricultural formulations is well known. See, e.g., U.S. Pat. No. 4,755,207 to Bannon at Columns 3–4. It will be appreciated that the host cell applied may be in any suitable form, including spores.

Solid and liquid compositions may be prepared by any conventional procedure which does not affect the viability of the active agent. Thus compositions of the present invention may be formulated as a solid, comprising the active agent and a finely divided solid carrier. Alternatively, the active agent may be contained in a liquid composition, including dispersions, emulsions and suspensions thereof.

The active agent of the present invention may be applied to substrates such as agricultural fields by any suitable means, such as dusting or spraying. The active agent can be applied as an aerosol, e.g., by dispersal in the air by means of a compressed gas or aerosol propellant, including, but not limited to, dichlorodifluoromethane and trichlorofluoromethane.

The active agent may be applied alone or in combination with inert solids such as a dust or suspended in a liquid solution such as an organic solvent (particularly non-phytotoxic oils) or an aqueous solution. The active agent may be combined and applied with adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour, and lignin.

The active agent may be combined and applied with surfactants, including anionic, cationic, and nonionic agents.

The amount of active agent in the composition is not critical, and will depend upon factors such as whether the active agent is living or nonliving, soil and atmospheric conditions, and the application technique employed. Typically, the active agent may comprise anywhere from about 0.001% by weight to about 50% by weight of the composition.

G. Combination Treatment Strategies

Also disclosed herein, as noted above, are combination treatments which involve combating insects in a location such as an agricultural field, forest or swamp by (a) applying to that location an insecticide effective against that insect, and (b) applying to that location either (i) an insect detoxication protein in an amount effective to degrade the applied insecticide, or (ii) a microbial cell as described above in an amount effective to degrade the applied insecticide (of course, detoxication proteins and cells expressing detoxication proteins may optionally be applied in combination). The term "agricultural field" is used herein to describe any plant growth substrate planted with an essentially uniform stand of plants, such as cotton, wheat, corn, soybean, and tobacco fields; greenhouses (e. g., containing Poinsettia); and rice paddies. Application of the insecticide may be carried out in accordance with known techniques, and application of the insecticide-degrading agent may be carried out as described hereinabove.

Any suitable insecticide may be applied, including, but not limited to, organophosphorus insecticides (e.g., S,S,S-tributy phosphorotrithiote, malathion, acephate, methyl parathion, methidathion, diazinon, azinphosmethyl, and monocrotphos), carbamate pesticides (e.g., thiodicarb), pyrethroid pesticides (e.g., cypermethrin), and other insecticides such as DDT, endrin, carbaryl, parathion, and EPN.

The two applying steps are carried out concurrently (i.e., are carried out sufficiently contemporaneously in time to combat soil contamination with the applied pesticide). For example, the two steps may be carried out simultaneously; the step of applying the insecticide may be carried out first and the step of applying the insecticide-degrading agent may be carried out a day, a week, or a month or more thereafter; or the step of applying the insecticide-degrading agent may be carried out first (preferably when the insecticide-degrading agent is a microorganism as described herein) and the step of applying the insecticide may be carried out a day, a week, or a month or more thereafter. Both applying steps may be carried out during the same growing season, or, where the insecticide-degrading agent is a microorganism, the agricultural field may be innoculated once with the microorganism to establish a persistent culture of that microorganism in that field (e. g., for a period of up to ten years or more) and the insecticide applied in growing seasons subsequent to the innoculation.

The present invention is explained in greater detail in the following non-limiting examples. Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right.

EXAMPLE 1 cDNA Cloning of Resistance-Associated Cytochrome p450 From the Tobacco Budworm The expression vector pKKHC and *E. coli* strain JM109 are used for expression of Tobacco Budworm (*Heliothis virescens* (F)) fat body P450.

Insects are obtained from commercial tobacco fields in Hebert, La., USA, where insecticide control failures with the insecticide Larvin have occurred. Resistance of this insect population is associated with extremely high levels of monooxygenase activity. Further, immunoblotting with a monoclonal antibody derived from resistance-associated P450 in *Drosolphila* (courtesy Larry Waters, Oak Ridge National Laboratories) showed it to bind specifically to a protein in fat body microsomes of the resistant population. This protein was not expressed in the fat body of susceptible insects.

This system was utilized to express P450 IIE1 (Larson et al., *J. Biol. Chem.* 266, 7321–7324 (1991)). The vector pKKHC is derived from pKK233-2 (Pharmacia LKB Biotechnology Inc.), which uses the IPTG-inducible trc promoter. The pBR322 origin of replication found in pKK233-2 is replaced with that from a pUC-derived plasmid in order to increase the plasmid copy number (Larson et al., *J. Biol. Chem.* 266, 7321–7324 (1991)).

To obtain correct spacing between the start codon copy number (Larson et al., *J. Biol. Chem.* 266, 7321–7324 (1991)), pKKHC site directed mutagenesis (T. A. Kunkel, *Proc. Natl. Acad. Sci. U.S.A.* 82, 488–492 (1985)) may be used to create an NcoI restriction site at the translation start site of the cDNA. The amino-terminal coding sequence has been shown to play an important role in *E. coli* expression levels (Barnes et al., *Proc. Natl. Acad. Sci. U.S.A.* 84, 4073–4077 (1991)). In particular, the second codon appears to be important for the expression the lacZ gene, and other codons at the N-terminus may be made more rich in adenosine and uridine nucleotides to more closely mimic mRNA's of *E. coli* (Barnes et al., *Proc. Natl. Acad. Sci. U.S.A.* 84, 4073–4077 (1991)). Methods utilized for these changes in structure include site directed mutagenesis and polymerase chain reaction (PCR) mutagenesis using primers incorporating the desired sequences at the 5' and 3' ends (Higuchi et al., *Nucleic Acids Res.* 16, 7351–7367 (1988)). Modifications at the amino terminus have increased the level of protein expression for several proteins, including P450's, without interfering with enzyme activities (Fisher et al., *FASEB J.* 6, 759–764 (1992)). Following cloning of the altered cDNA into pKKHC, the correct sequence is confirmed by restriction mapping followed by dideoxy chain-termination sequence analysis.

Plasmids are transformed into *E. coli* strain JM109 and plated onto LB plates containing 100 µg/ml ampicillin. Single colonies grown overnight in LB media containing 50 µg/ml ampicillian (LB-Amp) are used to inoculate 200 ml LB-Amp cultures. After reaching optical densities of 0.5–0.6 ($OD_{600}$), IPTG is added to the cultures at room temperature and the culture grown overnight at 30° C. with gentle shaking. Variable incubation times after introduction of IPTG may be utilized for RNA isolation versus evaluation of spectral properties or enzymatic activities (Wada et al., *Archives Biochem. Biophys.* 290, 376–380 (1991)).

A modification of the procedure of Barnes et al. (1991) is utilized to obtain subcellular fractions. Cells are harvested by centrifugation, resuspended in lysis buffer (100 mM KCl, 50 mM KPi, pH 7.4, 1 mM EDTA) containing 1 mg/ml lysozyme, and incubated 30 minutes on ice. The resulting spheroplasts are collected by centrifugation, resuspended in lysis buffer, and sonicated on ice for 4×30 seconds. Unbroken cells are pelleted by centrifugation for 15 minutes at 2000 xg and the supernatant centrifuged for 60 minutes at 45,000 xg. The resulting pellet is resuspended in lysis buffer and washed by centrifugation for 20 minutes at 52,000 xg. The resulting particulate fraction is resuspended in 1 ml storage buffer (20% glycerol, 50 mM KPi, pH 7.5, 1 mM EDTA) and stored at −80° C. following freezing in liquid nitrogen.

It is uncertain as to whether P450 purification is required to characterize its expression by *E. coli*. In the absence of purification, Larson et al., *J. Biol. Chem.* 266, 7321–7324 (1991), and Lareson et al., *Proc. Natl. Acad. Sci. U.S.A.* 88, 9141–9145 (1991)) were unable to determine the concentration of expressed P450 2El from *E. coli* due to contamination by bacterial cytochromes o and d, whose CO spectra interfere with P450 quantitation. In another study, of three P450 cDNA constructs which produced immunologically reactive proteins, only one had catalytic activity. In this case, purification of one construct resulted in a P450 with catalytic activity and a CO difference spectrum (Li et al., *J. Biol. Chem.* 266, 19186–19191 (1991)). In contrast, other studies utilizing *E. coli* expression systems have been able to generate CO difference spectrum and catalytic activity without further purification steps (Fisher et al., *FASEB J.* 6, 759–764 (1992); Barnes et al., *Proc. Natl. Acad. Sci. U.S.A.* 88, 5597–5601 (1991)).

If purification is necessary for the successful expression of catalytic activity, a modification of methods described by Li et al., *J. Biol. Chem.* 266, 19186–19191 (1991), is utilized. Briefly, following the removal of cell debris, the supernatant is solubilized with sodium cholate or Emulgen 911. The supernatant is loaded on an octylamino-Sepharose 4B column equilibrated with buffer A (0.1M potassium phosphate pH 7.4, 0.5% sodium cholate, 0.1 mM EDTA, 0.1 mM DTT, 0.4 mM PMSF, and 20% glycerol), washed with buffer A, and eluted with buffer A containing 0.4% sodium cholate and 0.06% Lubrol PX. Peak fractions containing P450 are determined by absorbance spectra and immunoblot analysis using *Drosophila* antibody. These are pooled and dialyzed against buffer B (30 mM potassium phosphate, pH 7.4, 0.2% sodium cholate, 0.2% Emulgen 911, 0.1 mM EDTA, 0.1 mM DTT, 0.5 mM PMSF, and 20% glycerol) and loaded on a hydroxylapatite column. This column is washed with buffer B containing 50 mM potassium phosphate, and eluted with buffer B containing 180 mM potassium phasphate. The resulting P450 fractions are pooled, dialyzed against buffer C (10 mM potassium phasphate, pH 7.4, 0.1 mM EDTA, 0.1 mM DTT, and 20% glycerol) overnight and applied to another hydroxylapatite column to remove detergents. This column is washed with buffer C and elution accomplished with buffer C containing 360 mM potassium phosphate.

Proteins from the particulate fraction and from the purified extracts are separated in 8% polyacrylamide gels and stained with Coomassie Blue or transferred to nitrocellulose sheets (Towbin et al., *Proc. Natl. Acad. Sci. U.S.A.* 76, 4350 (1983)) and immunostained with the antibody to Drosophila P450. Visulatization of the Western blot is accomplished by means of the interaction of the primary antibody with biotinylated secondary antibody, followed by an avidin biotinylated horseradish peroxidase complex (VECTASTAIN™ ABC Kit) (Vector Laboratories).

Reduced CO difference spectra are carried out in intact bacteria as well as in isolated bacterial membranes as previously described (Omura et al., *J. Biol. Chem.* 239, 2370–2378 (1964)). Catalytic activity of solubilized membranes or of purified preparations is determined using the reconstituted enzyme system described by Levi and Hodgson, *Int. J. Biochem.* 15, 349 (1983). In this system, solubilized membranes or purified enzymes are added to mouse liver NADPH-cytochrome P450 reductase (prepared by the method of Yasukochi and Masers, *J. Biol. Chem.* 251, 5337 (1976)) and 1,2,-dilauroyl phosphatidylcholine (30 µg/ml, final concentration). Additional details of assay conditions for benzo(a)pyrene hydroxylation, p-nitroanisole O-demethylation, benzphetamine, N-demethylation, and methozyresorufin O-demethylation are in accordance with known procedures (R. Rose et al., *Pestic. Biochem. Physiol.* 99, 535 (1991)). Metabolism of $^{14}C$ labeled thiodicarb (Rhone Poulenc Chemical Company) is initiated by the addition of 50 moles thiodicarb to the 1 ml incubation medium described above. The reaction is terminated by addition of 1 ml ethanol following a 20 minute incubation period at 30° C. Following two chloroform extractions, the chloroform is evaporated and an aliquot applied to a silica gel plate. Parent and metabolites are separated using ethyl acetate: isopropyl ether (3:2) as a solvent system and the plates analyzed by means of a Berthold analyzer. Additional pesticides may also be selected for study, if warranted.

The *Vaccinia* virus system is an alternative expression system. The *Vaccinia* virus system is capable of expression of large amounts of enzymes (Gonzalez, *Pharmacol. Rev.* 40, 243–288 (1990)) and has been utilized to express a number of P450s in different mammalian cells in vitro (Aoyama et al., *Mol. Carcinogen.* 1, 253–259 (1989); Battula et al., *Proc. Natl. Acad. Sci. U.S.A.* 84, 4073–4077 (1987); Crespi et al., Carcinogenesis 12, 1197–1201 (1990)).

A partial cDNA sequence for resistance-associated P450 was initially determined and is given herein as SEQ ID NO:1. Sequence analysis revealed that the 5' end of the open reading frame was missing. It was estimated that an additional sequence of approximately 200–250 bases was necessary to have a complete reading frame encoding the P450. With this partial cDNA sequence, those skilled in the art will appreciate that other resistance-associated P450 cDNA sequences can be identified from other insect sources which can also be used to carry out the present invention.

EXAMPLE 2 cDNA Cloning of Esterase From Tobacco Budworm

RNA is isolated from tobacco budworms (*Heliothis virescens* (F)), using the RNA guanidinium thiocynate method of Chirgwin et al. (J. M. Chirgwin et al., *Biochemistry* 18, 5294 (1979). cDNA libraries are constructed using the lambda expression vector (R. A. Young etal., *Proc. Natl. Acad. Sci. U.S.A.* 80, 1194 (1983), and R. A. Young, *Science (U.S.A.)* 222,778 (1983)) and screened for the production of hydrolase fusion proteins using monospecific antibodies. Poly(A) RNA is purified from the total RNA on oligo (dT) cellulose using the Poly(A) Quik™ mRNA Isolation Kit (STRATAGENE®).

cDNA synthesis is conducted with a ZAP-cDNA® Synthesis Kit (STRATAGENE®) where 1st strand synthesis is initiated with a XhoI/poly T primer. The use of 5-methyl-dCTP during first strand synthesis eliminates the need for site-specific methylases, allowing cDNA construction within 24 hours. The addition of a XhoI linker on the 5' end and EcoRl on the 3' end allows for the unidirectional insertion of the cDNA into the Uni-ZAP XR vector proteins in the sense orientation. An additional advantage of Uni-ZAP™ XR is that fragments cloned into this vector can be automatically excised to generate subclones in the pBluescript SK-phagemid vector, eliminating the time involved in subcloning for sequence analysis. Expression is carried out in *E. coli* JM109 as described above.

The USB cDNA CLONSTRUCT™ method may also be used. This approach to cDNA cloning has the advantage of discriminating between partial and full-length clones, as well as defining the orientation of inserts. When first strand synthesis is incomplete, the resulting cDNA:mRNA hybrid has a 3' recessed end whereas completed synthesis approximates a blunt end. Terminal deoxynucleotidyl transferase acts more efficiently on blunt ends. Partial synthetic products are therefore inefficiently tailed, do not recircularize, and are excluded from the library.

Phage containing inserts from Uni-ZAP™ XR is packaged with the GIGAPACK II GOLD™ Lambda Packaging Kit (STRATAGENE®). In this system phage containing inserts generate an inactive β-galactosidase fusion protein. These phage can be distinguished from nonrecombinant phage by their inability to metabolize X-Gal in the presence of IPTG on a lac host. The specific control host strain is VCS257. Duplicate nitrocellulose lifts of recombinant phage induced with IPTG are screened using a picoBlue™ immunoscreening kit (Strategene). The nitrocellulose filters are screened with esterase specific rabbit antibody specific for the green peach aphid esterase obtained from A. Devenshire, pretreated with *Escherichia coli* lambda phage lysate to reduce nonspecific binding. The goat-anti rabbit conjugated alkaline phosphatase staining technique is used.

Positive clones are picked, amplified and subjected to at least two additional screenings. If the percent of the population of plaques which are positive is greatly increased, are white in the presence of IPTG and X-gal and have insert sizes (determined by PCR) appropriate to the size of the esterase protein, pBluescript will be excised for sequence analysis using Sequenase™ (US Biochemical). Sequencing is conducted by the dideoxy chain termination method of Sanger (J. Messing, *Methods Enzymol* 101, 20 (1983), and A. Smith *Methods Enzymol* 65 560 (1983)). Colonies are rescreened for positive identification of the pBluescript insert, the insert sized, and a restriction map constructed before the insert DNA is purified for sequencing. Sequence information is compared with protein sequence data to confirm the identity of the insert DNA and also compared to other proteins in GeneBank.

A cDNA encoding a *Heliothis virescens* resistance-associated esterase is obtained which encodes a protein having the first sixteen $NH_2$-terminal sequence of Asp Asp Glu Xaa Arg Glu Val Arg Thr Ala Gln Gly Pro Leu Arg Gly (SEQ ID NO:2), where "Xaa" represents an unknown amino acid residue.

EXAMPLE 3

Sequence of cDNA Clone or Resistance-Associated Cytochrome p450 From the Tobacco Budworm The partial sequence for resistance-associated P450 was initially determined as described in Example 1 and is given herein as SEQ ID NO:1. As noted in Example 1, it was estimated that an additional sequence of approximately 200–250 bases at the 5' end would be contained in the complete reading frame.

Further sequencing of resistance-associated P450 using techniques known in the art revealed an additional 224 bases at the 5' end of SEQ ID NO:1. The complete nucleotide sequence and predicted amino acid sequence for resistance-associated P450 are given herein as SEQ ID NO:3 and SEQ ID NO:4, respectively. Those skilled in the art will appreciate that this cDNA sequence will allow the identification of additional resistance-associated P450 cDNA sequences from other insect sources, which can also be used to carry out the present invention.

The foregoing examples are illustrative of the present invention, and are not to be construed as limiting thereof. The invention is defined by the following claims, with equivalents of the claims to be included therein.

That which is claimed is:

1. A cytochrome p450 protein comprising the sequence of SEQ ID NO:4.

2. Isolated and purified DNA encoding an insecticide resistance associated cytochrome P450, said DNA selected from, the group consisting of:
   (a) DNA encoding *Hellothis virescens* (F) insecticide resistance associated fat body cytochrome P450, comprising the sequence of SEQ ID NO:3.
   (b) insect DNA encoding a resistance associated cytochrome p450, which complementary strand remains hybridized to DNA of (a) above following a stringent wash of 0.3M NaCl, 0.03M sodium citrate, 0.1% SDS at 60° C.; and
   (c) DNA which encodes a resistance-associated cytochrome p450 encoded by (a) or (b) above and which differs from (a) or (b) due to the degeneracy of the genetic code.

3. Isolated and purified DNA, which encodes *Hellothis virescens* (F) insecticide resistance associated fat body cytochrome p450 and comprises the sequence of SEQ ID NO:3.

4. Isolated and purified DNA according to claim 2 in a recombinant cloning vector.

5. A microbial cell containing and expressing heterologous DNA encoding an insect detoxification protein, said heterologous DNA according to claim 2.

6. A microbial cell containing and expressing heterologous DNA encoding an insect detoxification protein, said heterologous DNA having the sequence of SEQ ID NO:3.

7. A microbial cell according to claim 5 or 6, wherein said microbial cell is a bacterium.

8. A microbial cell according to claim 7, wherein said microbial cell is selected from the group consisting of *Pseudomonas* and *Bacillus*.

* * * * *